United States Patent [19]

Mori et al.

[11] 4,111,879
[45] Sep. 5, 1978

[54] COMPOSITION FOR INHIBITING ADHESION OF SHELLFISH AND ALGAE

[75] Inventors: Kogoro Mori, Shimizu; Taro Izawa; Yoshifumi Mizuno, both of Shizuoka; Sadayoshi Matsui, Shimizu, all of Japan

[73] Assignee: Ihara Chemical Industry Co., Ltd., Tokyo, Japan

[21] Appl. No.: 736,339

[22] Filed: Oct. 28, 1976

[30] Foreign Application Priority Data

Jul. 10, 1976 [JP] Japan ................ 51-81476

[51] Int. Cl.$^2$ .................... C09D 5/14; C09D 5/16
[52] U.S. Cl. .................... 260/29.6 N; 106/15 R; 106/16; 260/29.6 MN; 260/30.2; 428/907
[58] Field of Search ................ 106/15 R, 16; 260/29.6 MN, 29.6 N, 326.5 FM, 326.5 S, 326.41, 30.2; 428/907

[56] References Cited

U.S. PATENT DOCUMENTS

| | | | |
|---|---|---|---|
| 2,884,330 | 4/1959 | Goldblatt et al. | 106/15 R |
| 3,098,002 | 7/1963 | Riddell et al. | 260/326.5 FM |
| 3,223,513 | 12/1965 | Geary | 106/15 R |
| 3,265,708 | 8/1966 | Stiteler | 260/326.5 FM |
| 3,394,145 | 7/1968 | Bublitz | 260/326.5 FM |
| 3,465,001 | 9/1969 | Bolhofer et al. | 260/326.41 |
| 3,538,114 | 11/1970 | Himmele et al. | 260/326.41 |
| 3,575,123 | 4/1971 | Shepherd et al. | 106/15 R |
| 3,586,697 | 6/1971 | Ozaki et al. | 260/326.5 FM |
| 3,734,927 | 5/1973 | Kawada et al. | 260/326.5 FM |
| 3,743,654 | 7/1973 | Fujinami et al. | 260/326.5 FM |
| 3,821,247 | 6/1974 | Sturm et al. | 260/326.5 FM |
| 3,896,753 | 7/1975 | Shepherd et al. | 106/15 R |
| 4,010,182 | 3/1977 | Matsui et al. | 260/326.5 FM |

*Primary Examiner*—Ronald W. Griffin
*Attorney, Agent, or Firm*—Oblon, Fisher, Spivak, McClelland & Maier

[57] ABSTRACT

A composition for inhibiting an adhesion of shellfish and algae comprises a resin, a medium and a N-aryl-maleimide having the formula

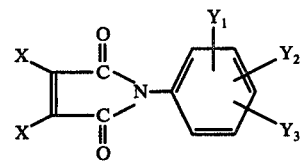

wherein X represents hydrogen or halogen atom; $Y_1$ represents hydrogen, or halogen atom or alkyl, lower alkoxy, nitro, hydroxyl, alkoxycarbonyl, carboxyl, phenyl, phenylamino, alkenyl, thiocyano, sulfone, acetylamino, or sulfamoyl group; $Y_2$ represents hydrogen or halogen atom or alkyl, lower alkoxy, nitro or hydroxyl group and $Y_3$ represents hydrogen or halogen atom or dialkylamino group.

The inhibiting composition is coated on a fishing net, a ship bottom or other apparatus in water.

2 Claims, No Drawings

COMPOSITION FOR INHIBITING ADHESION OF SHELLFISH AND ALGAE

BACKGROUND OF THE INVENTION

The present invention relates to a shellfish and algae inhibiting composition which is coated on a ship bottom, a fishing net, apparatus, in sea such as a buoy for wave generator, a construction in water such as a dam apparatus, a waterway for cooling water used in a condenser of a heat power plant or in a heat-exchanger for petrochemical plants.

It has been known that various shellfish and algae such as Balanus, Ostrea, Mytilus, Hydrozoa, Styela, Bugula, Ulva, Enteromorpha, Ectocarpus, etc.. have been bred on the surfaces in water such as the ship bottom, the apparatus in water, the construction in water, the waterway for cooling water and the like.

These shellfish and algae cause the increase of flow resistance and the decrease of heat conductivity to disadvantageously decrease the functions of the apparatus.

For example, taking the ship, the decrease of the speed and the excess consumption of the fuel are caused. Moreover, in order to clean the ship bottom, the loss for the suspension of the ship service is caused and the cost for the cleaning is needed. These are remarkable economical loss.

In the constractions in water, the handling trouble is caused.

In the waterway for cooling water used in the condenser or the heat exchanger, the rate of water supply is decreased to decrease the cooling coefficient, and the function of the condenser or the heat exchanger is damaged by shellfish or algae mass which are peeled off from the wall of the waterway. These are also remarkable economical loss.

In order to prevent such trouble caused by the breeding and the adhesion of shellfish and algae in sea water or fresh water, it has been proposed to use paints containing a heavy metal compound such as copper oxides, mercury oxides; an organo-tin oxide; an organic chlorine-containing compound and an organic sulfur-containing compound, or an arsenic compound such as phenarsazine chloride etc..

In the waterway for the cooling water, chlorine or formaline is directly added in the water to prevent the breeding and the adhesion of shellfish and algae.

However, the inhibiting compositions containing the heavy metal compound such as copper oxides and mercury oxides have low stability in a storage because the heavy metal compound is reactive to the resin component in the composition.

In the polluted sea such as harbor to which industrial discharged water is flowed, hydrogen sulfide is generated by microorganism in the polluted sea and the heavy metal compound is discolored and deteriorated to lose the effect.

The copper compounds and the mercury compounds are effective against shellfish such as Balanus, Ostrea, Mytilus, Hydrozoa, Styela, Bugula, etc., however, they are not effective against algae.

When the inhibiting composition is coated on a substrate made of light metal such as aluminum and aluminum-magnesium, the heavy metal such as copper and mercury is deposited on the substrate to electrochemically accelerate the corrosion of the substrate. This is the other disadvantage.

The inhibiting compositions containing the organo-tin compound such as tributyl tin oxide have inferior effect to those of the inhibiting compositions containing the copper compound or the mercury compound, and also they are expensive. When a large amount of the organo-tin compound is mixed, the characteristics of the coated film is deteriorated and bad smell is caused in the handling.

The inhibiting compositions containing the organic chlorine-containing compound or the organic sulfur-containing compound have inferior effects comparing with the other inhibiting compositions. For example, even though they are effective for Bugula, they are not effective for Balanus. They are only effective for certain shellfish or algae whereby it is difficult to use them in practical applications.

The inhibiting composition containing phenarsazine chloride has been used. However phenarsazine chloride is toxic to human body, and stimulates mucous membrane whereby the preparation of the composition and the coating operation are not easy. When chlorine or formaline is added to water in the waterway for the cooling water, the cooling apparatus is corroded and the effect for inhibiting the adhesion of shellfish and algae is not remarkable.

These conventional active ingredients are toxic to human body and fish, whereby the application is limited.

In the specification, the composition for inhibiting an adhesion of shellfish and algae is referred as the shellfish-algae inhibiting composition.

SUMMARY OF THE INVENTION

It is an object of the present invention to overcome the disadvantages of the conventional composition for inhibiting an adhesion of shellfish and algae, and to provide a shellfish algae inhibiting composition which has low toxicity to fish and no toxicity to animals and which imparts excellent effect for inhibiting the adhesion of shellfish and algae for a long term even in a polluted sea.

Another object of the invention is to provide a shellfish-algae inhibiting composition which does not electrochemically corrode light metal substrate such as aluminum and magnesium and which does not corrode a cooling apparatus in a waterway, and which inhibit an adhesion and a breeding of shellfish and algae.

These objects of the invention have been attained by providing a composition for inhibiting an adhesion of shellfish and algae which comprises a resin, a medium and a N-arylmaleimide having the formula

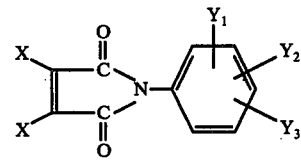

Wherein X represents hydrogen or halogen atom; $Y_1$ represents hydrogen, or halogen atom or alkyl, lower alkoxy, nitro, hydroxyl, alkoxycarbonyl, carboxyl, phenyl, phenylamino, alkenyl, thiocyano, sulfone, acetylamino or sulfamoyl group; $Y_2$ represents hydrogen, or halogen atom or alkyl, lower alkoxy, nitro or hydroxyl group and $Y_3$ represents hydrogen or halogen atom or dialkylamino group.

DETAILED DESCRIPTION OF THE EMBODIMENTS

The N-arylmaleimide can be produced by reacting a maleic anhydride having the formula

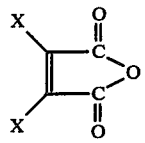

[II]

wherein X represents hydrogen or halogen atom; with an arylamine having the formula

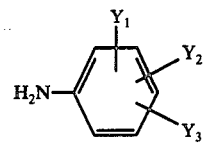

[III]

wherein $Y_1$, $Y_2$ and $Y_3$ are defined above, and then dehydrating the resulting N-arylmaleamide for a cyclization in the presence of an acid catalyst, without separating the N-arylmaleamide from the reaction mixture.

Suitable N-arylmaleimides having the formula [I] which are used as effective shellfish and algae inhibiting agent in the invention are shown in Table 1, wherein the substituents X, $Y_1$, $Y_2$ and $Y_3$ are shown. The compound numbers are referred in the following examples.

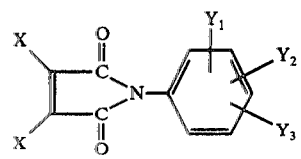

[I]

| Compound No. | N-aryl maleimide [I] | Substituent X | $Y_1$ | $Y_2$ | $Y_3$ | Melting point (° C) |
|---|---|---|---|---|---|---|
| 1 | N-phenylmaleimide | H | H | H | H | 88 – 90 |
| 2 | N-(2-chlorophenyl)maleimide | H | 2 - Cl | H | H | 72 – 74.5 |
| 3 | N-(3-chlorophenyl)maleimide | H | 3 - Cl | H | H | 90 – 92 |
| 4 | N-(4-chlorophenyl)maleimide | H | 4 - Cl | H | H | 109 – 110 |
| 5 | N-(3-bromophenyl)maleimide | H | 3 - Br | H | H | 127 – 130 |
| 6 | N-(4-iodophenyl)maleimide | H | 4 - I | H | H | 157 – 161 |
| 7 | N-(4-fluorophenyl)maleimide | H | 4 - F | H | H | 151 – 153 |
| 8 | N-(o-tolyl)maleimide | H | 2 - $CH_3$ | H | H | 74 – 76 |
| 9 | N-(p-tolyl)maleimide | H | 4 - $CH_3$ | H | H | 164 – 165 |
| 10 | N-(4-n-butylphenyl)maleimide | H | 4 - $C_4H_9$ | H | H | 168 – 170 |
| 11 | N-(4-dodecylphenyl)maleimide | H | 4 - $C_{12}H_{25}$ | H | H | 67 – 68 |
| 12 | N-(3-methoxyphenyl)maleimide | H | 3 - $CH_3O$ | H | H | 62 – 64 |
| 13 | N-(4-ethoxyphenyl)maleimide | H | 4 - $C_2H_5O$ | H | H | 135 – 137 |
| 14 | N-(3-isopropoxyphenyl)maleimide | H | 3- $CH(CH_3)_2$-CHO | H | H | b.p. 179–180/3 mmHg |
| 15 | N-(2-nitrophenyl)maleimide | H | 2 - $NO_2$ | H | H | 120 – 122 |
| 16 | N-(3-nitrophenyl)maleimide | H | 3 - $NO_2$ | H | H | 126 – 128 |
| 17 | N-(4-nitrophenyl)maleimide | H | 4 - $NO_2$ | H | H | 164.5 – 166 |
| 18 | N-(4-hydroxyphenyl)maleimide | H | 4 - OH | H | H | 187 – 189 |
| 19 | N-(2-carboxyphenyl)maleimide | H | 2 - COOH | H | H | 147 – 155 |
| 20 | N-(o-biphenylyl)maleimide | H | 2-$C_6H_5$ | H | H | 139 – 140 |
| 21 | N-(p-biphenylyl)maleimide | H | 4-$C_6H_5$ | H | H | 139 – 141 |
| 22 | N-(anilinophenyl)maleimide | H | 4-NH-$C_6H_5$ | H | H | 130 – 131 |
| 23 | N-(3-vinylphenyl)maleimide | H | 3—CH=$CH_2$ | H | H | 100 – 102 |
| 24 | N-(4-vinylphenyl)maleimide | H | 4—CH=$CH_2$ | H | H | 118 – 120 |
| 25 | N-(4-thiocyanophenyl)maleimide | H | 4 - SCN | H | H | 79 – 80 |
| 26 | N-(4-sulfophenyl)maleimide | H | 4 - $SO_3H$ | H | H | 112 |
| 27 | N-(4-acetylaminophenyl)maleimide | H | 4-$NHCOCH_3$ | H | H | 217 – 218 |

-continued

| Compound No. | N-aryl maleimide [I] | Substituent X | $Y_1$ | $Y_2$ | $Y_3$ | Melting point (°C) |
|---|---|---|---|---|---|---|
| 28 | N-(2,3-dichlorophenyl) maleimide | H | 2 - Cl | 3 - Cl | H | 97 – 98 |
| 29 | N-(2,5-dichlorophenyl) maleimide | H | 2 - Cl | 5 - Cl | H | 122 – 123 |
| 30 | N-(3,4-dichlorophenyl) maleimide | H | 3 - Cl | 4 - Cl | H | 171 – 172 |
| 31 | N-(3,5-dichlorophenyl) maleimide | H | 3 - Cl | 5 - Cl | H | 136 – 137 |
| 32 | N-(2-chloro-4-nitrophenyl) maleimide | H | 4 - $NO_2$ | 2 - Cl | H | 141 – 142 |
| 33 | N-(4-chloro-2-nitrophenyl) maleimide | H | 2 - $NO_2$ | 4 - Cl | H | 169 |
| 34 | N-(4-chloro-2-hydroxy phenyl) maleimide | H | 2 - OH | 4 - Cl | H | 172 – 175 |
| 35 | N-(2,3-xylyl) maleimide | H | 2 - $CH_3$ | 3 - $CH_3$ | H | 118 – 120 |
| 36 | N-(2,4-xylyl) maleimide | H | 2 - $CH_3$ | 4 - $CH_3$ | H | 106 – 107 |
| 37 | N-(2,5-xylyl) maleimide | H | 2 - $CH_3$ | 5 - $CH_3$ | H | 82 – 83 |
| 38 | N-(3,5 xylyl) maleimide | H | 3 - $CH_3$ | 5 - $CH_3$ | H | 85 – 86.5 |
| 39 | N-(4-methyl-3-nitrophenyl maleimide | H | 3 - $NO_2$ | 4 - $CH_3$ | H | 102 |
| 40 | N-(2-methyl-3-nitrophenyl) maleimide | H | 3 - $NO_2$ | 2 - $CH_3$ | H | 167 – 168 |
| 41 | N-(2,5-dimethoxyphenyl) maleimide | H | 2 - $CH_3O$ | 5 - $CH_3O$ | H | 122 |
| 42 | N-(4-ethoxy-2-nitrophenyl) maleimide | H | 2 - $NO_2$ | 4 - $C_2H_5O$ | H | 83 |
| 43 | N-(3-carboxy-4-hydroxyphenyl) maleimide | H | 3 - COOH | 4 - OH | H | 214 – 222 |
| 44 | N-(4-carboxy-3-hydroxyphenyl) maleimide | H | 4 - COOH | 3 - OH | H | 239 – 243 |
| 45 | N-(2,4,6-trichlorophenyl) maleimide | H | 2 - Cl | 4 - Cl | 6 - Cl | 130 – 132 |
| 46 | N-(4-dimethylamino-3,5-dinitrophenyl) maleimide | H | 3 - $NO_2$ | 4 - $NO_2$ | 4-$N(CH_3)_2$ | |
| 47 | N-phenyl-2,3-dichloromaleimide | Cl | H | H | H | 208 – 210 |
| 48 | N-phenyl-2,3-dibromomaleimide | Br | H | H | H | 165 |
| 49 | N-phenyl-2,3-difluoromaleide | F | H | H | H | 88 – 90 |
| 50 | N-(2-chlorophenyl)-2,3-dichloro maleimide | Cl | 2 - Cl | H | H | 132 |
| 51 | N-(3-chlorophenyl)-2,3-dichloro maleimide | Cl | 3 - Cl | H | H | 183 |
| 52 | N-(4-chlorophenyl)-2,3-dichloromaleimide | Cl | 4 - Cl | H | H | 210 – 216 |
| 53 | N-(4-iodophenyl)-2,3 dichloromaleimide | Cl | 4 - I | H | H | 251 – 254 |
| 54 | N-(4-chlorophenyl)-2,3-difluoromaleimide | F | 4 - Cl | H | H | 74 – 76 |
| 55 | N-(p-tolyl)-2,3-dibromomaleimide | Br | 4 - $CH_3$ | " | " | 174 |
| 56 | N-(4-methoxyphenyl)-2,3-dichloromaleimide | Cl | 4 - $CH_3O$ | " | " | 209 – 210 |
| 57 | N-(4-nitrophenyl)-2,3-dibromomaleimide | Br | 4 - $NO_2$ | " | " | 207 – 208 |
| 58 | N-(4-ethoxycarbonylphenyl)-2,3-dichloromaleimide | Cl | 4 - $COOC_2H_5$ | " | " | 305 |
| 59 | N-(2-carboxyphenyl)-2,3-dichloromaleimide | Cl | 2 - COOH | " | " | 327 – 329 |
| 60 | N-(3-carboxyphenyl)-2,3-dichloromaleimide | Cl | 3 - COOH | " | " | 238 – 240 |
| 61 | N-(4-carboxyphenyl)-2,3-dichloromaleimide | Cl | 4 - COOH | " | " | 305 |
| 62 | N-(4-thiocyanophenyl)-2,3-dichloromaleimide | Cl | 4 - SCN | " | " | 205 – 208 |
| 63 | N-(4-sulfamoylphenyl)-2,3-dichloromaleimide | Cl | 4 - $SO_2NH_2$ | " | " | 300 |
| 64 | N-(3,4-dichlorophenyl)-2,3-dichloromaleimide | Cl | 3 - Cl | 4 - Cl | " | 206 – 208 |
| 65 | N-(2-chloro-4-methoxycarbonylphenyl)-2,3-dichloromaleimide | Cl | 4 - $COOCH_3$ | 2 - Cl | H | 156 – 157 |
| 66 | N-(2,5-xylyl)-2,3-dichloromaleimide | Cl | 2 - $CH_3$ | 5 - $CH_3$ | H | 127 – 129 |
| 67 | N-(2-methyl-6-methoxycarbonylphenyl)-2,3-dichloromaleimide | Cl | 6 - $COOCH_3$ | 2 - $CH_3$ | H | 121 – 122 |

The N-arylmaleimides having the formula [I] which is used as an active ingredient for shellfish and algae inhibiting composition in the invention can be produced by reacting an maleic anhydride having the formula [II] with an arylamine having the formula [III] with or without a solvent at 20° to 100° C. for 0.5 to 2 hours and then, dehydrating the resulting N-arylmaleamide [IV] for a cyclization in the presence of an acid catalyst at 80° to 200° C. for 1 to 10 hours, without separating the N-arylmaleamide [IV] from the reaction mixture, as shown in the following reaction formula.

Reaction formula 1

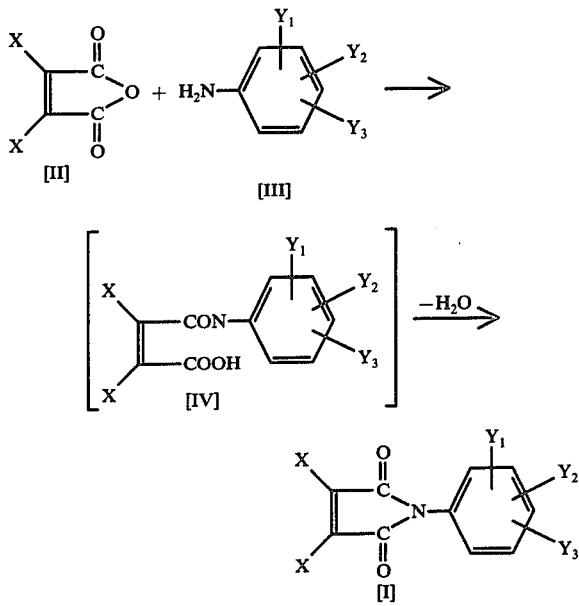

In the formula, X, $Y_1$, and $Y_2$, and $Y_3$ are defined above.

When the reaction is carried out in a solvent, an inert solvent is used.

Suitable solvents include aliphatic hydrocarbons such as octane, decane, ligroin and cyclohexane; aromatic hydrocarbons such as benzene, toluene, xylene, ethyl benzene, diisopropyl benzene, solvent naptha; haloaromatic hydrocarbons such as chlorobenzene, dichlorobenzene, chlorotoluene and chloroisopropyl benzene; ethers such as n-butyl ether, dissoamyl ether and dioxane; nitriles such as acetonitrile, propionitrile, and benzonitrile; and ketones such as methylethyl ketone and methyl isobutyl ketone.

The acid catalyst can be conventional dehydrating agents.

Suitable acid catalysts include hydrochloric acid, sulfuric acid, sulfur trioxide, trifluoroacetic acid, trifluoromethanesulfonic acid, phosphoric acid, acetic anhydride, thionyl chloride, phosphorus oxychloride and toluenesulfonic acid.

The amount of the acid catalyst is in a range of 0.01 to 0.3 mole per 1 mole of the maleic anhydride [II].

Suitable maleic anhydride having the formula [II] used as the starting material, include maleic anhydride, 2,3-difluoromaleic anhydride, 2,3-dichloromaleic anhydride, and 2,3-dibromomaleic anhydride.

Suitable aromatic amines used as the other starting material include aniline, haloanilines, alkylanilines, lower alkoxyanilines, nitroanilines, hydroxyanilines, alkoxycarbonylanilines, carboxyanilines, phenylanilines, phenylaminoanilines, alkenylanilines, thiocyanoanilines, sulfoneanilines, acetylaminoanilines, sulfamoylanilines, dihaloanilines, dialkylanilines, di(-lower alkoxy) anilines, halo-nitroanilines, halo-hydroxyanilines, alkyl-nitroanilines, alkyl-alkoxycarbonylanilines, nitro-lower alkoxyanilines, carboxyl-hydroxyanilines, trihaloanilines and N,N-dialkylaminodinitroanilines.

The amount of the aromatic amine III is usually equimole to the maleic anhydride II and can be more than equimole to it.

The preparation of the N-arylmaleimides of the invention will be illustrated by certain examples.

Preparation 1

In a 500 ml four necked flask equipped with a thermometer, a condenser having a water separator, a dropping funnel and a stirrer, 150 ml of xylene was charged and 19.6 g (0.2 mole) of maleic anhydride was dissolved.

Then a solution of 25.5 g (0.2 mole) of 4-chloroaniline in 100 ml of xylene was added dropwise to the solution at room temperature with stirring. The exothermic reaction was caused. The reaction was carried out with stirring at 60° to 68° C. for 2 hours after the addition.

Then, 1.0 g (0.0097 mole) of sulfuric acid was added to the former reaction mixture. The reaction was carried out with stirring at 135° to 138° C. for 4 hours under the azeotropical distillation.

After the reaction, xylene was distilled off, and the reaction mixture was poured into 500 ml of water and the precipitate was separated by a filtration. The product was recrystallized from ethanol to obtain 36.5 g of N-(4-chlorophenyl)maleimide having a melting point of 109° to 110° C. (yield 88.1%).

Preparations 2 to 8

In accordance with the process of Preparation 1, various N-arylmaleimides were produced by reacting various maleic anhydride with various aromatic amines in various solvents, and then dehydrating the products for the cyclization.

The results are shown in Table 2.

Table 2

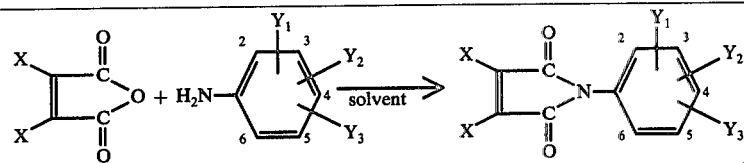

| Prep. No. | Starting Materials | | Reaction Solvent (ml) | Acid catalyst (g) | Additional reaction | | Cyclization in dehydration | |
| | Maleic anhydrides (g) | Aromatic amines (g) | | | Temp. (° C) | Time (hr.) | Temp. (° C) | Time (hr.) |
| --- | --- | --- | --- | --- | --- | --- | --- | --- |
| 2 | X = H (19.6) | $Y_1$ = 4 - $NO_2$ $Y_2$ = H $Y_3$ = H (27.6) | xylene (300) | sulfuric acid (1) | 65 - 70 | 2 | 137 - 140 | 4 |
| 3 | X = H (19.6) | $Y_1$ = 3-Cl $Y_2$ = 5 - Cl | ethylbenzene (300) | sulfuric acid (1) | 60 - 65 | 2 | 135 - 137 | 5 |

Table 2-continued

| Prep. No. | X | Y | Solvent | Catalyst | Temp | Time | M.P. | Yield |
|---|---|---|---|---|---|---|---|---|
| 4 | X = H (19.6) | $Y_1$ = 4-OH, $Y_2$ = H, $Y_3$ = H (32.4) | dioxane (300) | trifluoroacetic acid (0.5) | 50 – 55 | 2 | 98 – 101 | 6 |
| 5 | X = H (19.6) | $Y_1$ = 4-NH—, $Y_2$ = H, $Y_3$ = H (36.8) | toluene (300) | sulfuric acid (1.0) | 55 – 60 | 2 | 50 – 100 | 5 |
| 6 | X = H (19.6) | $Y_1$ = H, $Y_2$ = H, $Y_3$ = H (18.6) | chlorobenzene (300) | hydrochloric acid (2.0) | 50 – 55 | 2 | 130 – 132 | 6 |
| 7 | X = H (19.6) | $Y_1$ = 2-CH$_3$, $Y_2$ = H, $Y_3$ = H (21.4) | benzonitrile (300) | thionyl chloride (0.5) | 60 – 65 | 2 | 190 | 3 |
| 8 | X = H (19.6) | $Y_1$ = 3-CH$_3$, $Y_2$ = 5-CH$_3$, $Y_3$ = H (24.2) | xylene (300) | sulfuric acid) (1.0) | 70 – 75 | 2 | 137 – 140 | 3.5 |
| 9 | X = H (19.6) | $Y_1$ = 3-CH=CH$_2$, $Y_2$ = H, $Y_3$ = H (23.8) | xylene (300) | phosphorus oxychloride (1.0) | 35 – 42 | 2 | 137 – 140 | 4 |
| 10 | X = H (19.6) | $Y_1$ = 2-COOH, $Y_2$ = H, $Y_3$ = H | 1,2-diethoxy-ethane (300) | hydrochloric acid (2.0) | 50 – 53 | 2 | 123 – 125 | 7 |
| 11 | X = H (19.6) | $Y_1$ = 4—, $Y_2$ = H, $Y_3$ = H (33.8) | dichlorobenzene (300) | sulfur trioxide (0.5) | 60 – 65 | 2 | 174 – 175 | 3 |
| 12 | X = H (19.6) | $Y_1$ = 2-CH$_3$O, $Y_2$ = 5-CH$_3$O, $Y_3$ = H (30.6) | toluene (300) | hydrochloric acid (2.0) | 54 – 58 | 2 | 108 – 110 | 4 |
| 13 | X = Cl (33.4) | $Y_1$ = 4-Cl, $Y_2$ = H, $Y_3$ = H (25.5) | solvent naphtha (300) | sulfuric acid (1.0) | 40 – 48 | 2 | 130 – 135 | 5 |
| 14 | X = F (26.8) | $Y_1$ = H, $Y_2$ = H, $Y_3$ = H (18.6) | xylene (300) | p-toluene-sulfonic acid (0.5) | 50 – 55 | 2 | 137 – 140 | 3 |
| 15 | X = Cl (33.4) | $Y_1$ = 2-CH$_3$, $Y_2$ = 5-CH$_3$, $Y_3$ = H (24.2) | xylene (300) | thionyl chloride (0.5) | 60 – 63 | 2 | 138 – 140 | 3.5 |
| 16 | X = Cl (33.4) | $Y_1$ = 4-SCN, $Y_2$ = H, $Y_3$ = H (30.0) | xylene (300) | sulfuric acid (1.0) | 50 – 56 | 2 | 137 – 140 | 3 |
| 17 | X = Cl (33.4) | $Y_1$ = 4-COOC$_2$H$_5$, $Y_2$ = H, $Y_3$ = H | methylethyl ketone (300) | sulfuric acid (1.0) | 58 – 62 | 2 | 80 | 5 |
| 18 | X = Br (25.6) | $Y_1$ = 4-NO$_2$, $Y_2$ = H, $Y_3$ = H | xylene (300) | trifluoromethane sulfone (1.0) | 50 – 55 | 2 | 137 – 140 | 4 |

| Prep. No. | | Reaction products Amount (g) | Yield (%) | Melting point (° C) |
|---|---|---|---|---|
| 2 | X=H, $Y_1$=4-NO$_2$, $Y_2$=H, $Y_3$=H N-(4-nitrophenyl)maleimide | 37.1 | 85.0 | 164.5 – 166.0 |
| 3 | X=H, $Y_1$=3-Cl, $Y_2$=5Cl, $Y_3$=H, N-(3,5-dichlorophenyl)maleimide | 43.1 | 89.2 | 136 – 137 |
| 4 | X=H, $Y_1$=4-OH, $Y_2$=H, $Y_3$=H N-(4-anilinophenyl) maleimide | 31.8 | 84.0 | 187 – 189 |
| 5 | X = H, $Y_1$ = 4—NH—, $Y_2$ = H, $Y_3$=H N-(4-anilinophenyl)maleimide | 45.3 | 85.3 | 130 – 131 |
| 6 | X=H, $Y_1$=H, $Y_2$=H, $Y_3$=H N-phenyl maleimide | 28.8 | 83.2 | 88 – 90 |
| 7 | X=H, $Y_1$=2-CH$_3$, $Y_2$=H, $Y_3$=H N-o-tolyl maleimide | 30.3 | 80.9 | 74 – 76 |
| 8 | X=H, $Y_1$=3-CH$_3$, $Y_2$=5-C$_3$, $Y_3$=H N-(3,5-xylyl)maleimide | 33.2 | 82.6 | 85 – 86.5 |
| 9 | X=H, $Y_1$=3-CH=CH$_2$, $Y_2$H, $Y_3$H N-(3-vinylphenyl)maleimide | 31.6 | 79.5 | 100 – 102 |
| 10 | X=H, $Y_1$=2-COOH, $Y_2$=H, $Y_3$=H N-(2-carboxyphenyl)maleimide | 35.0 | 80.5 | 147 – 155 |

Table 2-continued

| | | | | |
|---|---|---|---|---|
| 11 | X = H, Y$_1$ = 4—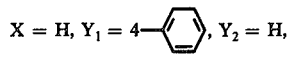, Y$_2$ = H, Y$_3$=H N-(p-biphenylyl)-maleimide | 41.7 | 83.7 | 139 – 141 |
| 12 | X=H, Y$_1$=2-CH$_3$O, Y$_2$=5-CH$_3$O Y$_3$=H N-(2,5-dimethoxyphenyl)maleimide | 38.2 | 81.6 | 122 |
| 13 | X=Cl, Y$_1$=4-Cl, Y$_2$=H, Y$_3$=H N-(4-chlorophenyl)-2,3-chloro maleimide | 45.0 | 81.5 | 210 – 216 |
| 14 | X=F, Y$_1$=H, N-phenyl-2,3-difluoromaleimide | 34.3 | 82.0 | 88 – 90 |
| 15 | X=Cl, Y$_1$=2-CH$_3$, Y$_2$=5-CH$_3$, Y$_3$=H, | 46.5 | 86.0 | 127 – 129 |
| 16 | X=Cl, Y$_1$=4-SCN, Y$_2$=H, Y$_3$=H N-(4-thiocyanophenyl)-2,3-dichloromaleimide | 48.9 | 81.8 | 205–208 |
| 17 | X=Cl, Y$_1$=4-COOC$_2$H$_5$, Y$_2$ =H. Y$_3$=H, N-(4-ethoxycarbonylphenyl)-2,3-dichloromaleimide | 52.1 | 83.0 | 197 – 200 |
| 18 | X-Br, Y$_1$=4-NO$_2$, Y$_2$=H, Y$_3$=H. N-(4-nitrophenyl)-2,3-dibromo-phenylmaleimide | 30.0 | 80.2 | 207 – 208 |

The shellfish-algae inhibiting agents of the invention can be used in a form of a coating compositions such as varnishes, paints, solutions and emulsions.

One or more N-arylmaleimides [I] are mixed with suitable film forming composition to prepare a shellfish-algae adhesion inhibiting paint. The paint is coated on the ship bottom or the construction in water or the inner wall of an apparatus for passing a cooling water, whereby the adhesion of shellfish or algae on the coated surface can be prevented.

The film forming compositions used in the purposes can be oil varnishes, synthetic resins, and synthetic rubbers. It is possible to blend suitable pigment and filler if desired, in the shellfish-algae inhibiting composition.

The N-arylmaleimide [I] is usually incorporated at a ratio of 5 to 80 wt.%, preferably 10 to 50 wt.% to the film forming composition.

In order to inhibit the adhesion and growth of shellfish and algae in the passage for the cooling water, it is possible to add the N-arylmaleimide in a form of emulsion, however, in order to maintain the effect for inhibiting the adhesion for a long time, it is necessary to coat a paint or varnish on the inner wall.

When the N-arylmaleimide of the invention is applied on the fishing net, the N-arylmaleimide and a resin are dissolved in an organic solvent to prepare a resin solution and a fishing net is immersed into the resin solution and the treated fishing net is dried.

In the preparation of the resin solution, the N-arylmaleimide [I] is incorporated at a ratio of 1 to 10 wt.%, preferably 1 to 6 wt.% and the resin is incorporated at a ratio of 5 to 15 wt.% preferably 7 to 12 wt.% in the organic solvent.

The effect is not substantially different, in the range of the concentration of the N-arylmaleimide [I].

The resins used in the preparation of the resin solution can be vinylchloride resins, phenol resins, alkyd resins, chlorinated rubber and the like.

The organic solvents can be benzene, toluene, xylene, chloroform and the like. When the resin is not easily soluble, 5 to 15 vol.% of dimethylformamide, dimethyl acetamide, dimethyl sulfoxide and the like is blended in the organic solvent.

The materials for the fishing nets for treating with the shellfish-algae inhibiting composition is not restricted, and the composition can be applied for the fishing net made of natural fibers, polyvinyl chloride, polyvinylalcohol, polyvinylidene chloride, polyfluoroethylene, polyamide, polyethylene, polypropylene, polystyrene, polyacrylonitrile and the like.

The effects of the N-arylmaleimides [I] of the invention for inhibiting the adhesion of shellfish and algae will be illustrated by certain inhibiting tests of the coated products coated with the compositions containing the N-arylmaleimides [I].

Composition 1

The compound No. 1 of N-phenyl-maleimide was mixed in the following components and the mixture was pulverized and blended by a pocket mill to prepare shellfish-algae adhesion inhibiting composition.

| | |
|---|---|
| Compound No. 1 | 20.0 wt.% |
| Red oxide | 10.0 wt.% |
| Talc | 15.0 wt.% |
| Barium sulfate | 20.0 wt.% |
| vinyl resin | 5.5 wt.% |
| Rosin | 5.5 wt.% |
| Tricresylphosphate | 2.0 wt.% |
| Methyl isobutyl ketone | 11.0 wt.% |
| Xylene | 11.0 wt.% |
| Total | 100.0 wt.% |

Composition 2

The compound No. 2 of N-(2-chlorophenyl)maleimide was mixed in the following components, and the mixture was pulverized and blended by a pocket mill to prepare shellfish-algae adhesion inhibiting composition.

| | |
|---|---|
| Compound No. 2 | 15.0 wt.% |
| Red oxide | 18.0 wt.% |
| Talc | 10.0 wt.% |
| Aluminum stearate | 0.5 wt.% |
| Graphite | 0.5 wt.% |
| Rosin | 26.0 wt.% |
| Boiled oil | 12.0 wt.% |
| Solvent naphtha | 18.0 wt.% |
| Total | 100.0 wt.% |

Test 1

Shellfish-Algae Inhibiting Test (1) Preparation of sample plate and Test method.

Each steel plate (300 × 100 × 1mm) was precoated with a wash primer for one time and further coated with a ship bottom coating for two times. and further coated with a ship bottom coating for two times. Each plate was further coated with each composition (Paint composition 1 using various N-arylmaleimides shown by Compound No.) by a brush for two times to prepare the sample.

Each sample was fitted in a wooden frame and was dipped into sea from a raft for dipping at a depth of 1.5 m.

(2) Result

The samples dipped in sea were pulled up for each specific terms of 2, 4, 6, 8, 10 amd 12 months. The ratio of a shellfish-algae adhered area to the total area of the sample was shown by percentage.

The ratio of shellfish adhered area to the area of the sample and the ratio of algae adhered area to the total area of the sample were shown by percentage.

The results are shown in Table 3.

Table 3

| Term for dipping | 2 months | | | 4 months | | | 6 months | | | 8 months | | | 10 months | | | 12 months | | |
|---|---|---|---|---|---|---|---|---|---|---|---|---|---|---|---|---|---|---|
| Adhered shellfish and algae Compound No. | S | A | T | S | A | T | S | A | T | S | A | T | S | A | T | S | A | T |
| 1 | 0 | 0 | 0 | 0 | 0 | 0 | 5 | 0 | 5 | 15 | 0 | 15 | 30 | 0 | 30 | 40 | 10 | 50 |
| 2 | 0 | 0 | 0 | 0 | 0 | 0 | 0 | 0 | 0 | 10 | 0 | 10 | 20 | 0 | 20 | 30 | 10 | 40 |
| 3 | 0 | 0 | 0 | 0 | 0 | 0 | 0 | 0 | 0 | 0 | 0 | 0 | 6 | 0 | 6 | 12 | 1 | 13 |
| 4 | 0 | 0 | 0 | 0 | 0 | 0 | 2 | 0 | 2 | 10 | 0 | 10 | 25 | 0 | 25 | 35 | 10 | 45 |
| 5 | 0 | 0 | 0 | 0 | 0 | 0 | 0 | 0 | 0 | 0 | 0 | 0 | 4 | 0 | 4 | 10 | 1 | 11 |
| 6 | 0 | 0 | 0 | 0 | 0 | 0 | 0 | 0 | 0 | 6 | 0 | 6 | 15 | 0 | 15 | 20 | 10 | 30 |
| 7 | 0 | 0 | 0 | 0 | 0 | 0 | 0 | 0 | 0 | 0 | 0 | 0 | 6 | 0 | 6 | 25 | 5 | 30 |
| 8 | 0 | 0 | 0 | 0 | 0 | 0 | 0 | 0 | 0 | 4 | 0 | 4 | 15 | 0 | 15 | 25 | 6 | 31 |
| 9 | 0 | 0 | 0 | 0 | 0 | 0 | 0 | 0 | 0 | 4 | 0 | 4 | 20 | 0 | 20 | 30 | 10 | 40 |
| 10 | 0 | 0 | 0 | 0 | 0 | 0 | 0 | 0 | 0 | 0 | 0 | 0 | 4 | 0 | 4 | 15 | 6 | 21 |
| 11 | 0 | 0 | 0 | 0 | 0 | 0 | 0 | 0 | 0 | 0 | 0 | 0 | 4 | 0 | 4 | 15 | 4 | 19 |
| 12 | 0 | 0 | 0 | 0 | 0 | 0 | 0 | 0 | 0 | 1 | 0 | 1 | 10 | 0 | 10 | 15 | 1 | 16 |
| 13 | 0 | 0 | 0 | 0 | 0 | 0 | 0 | 0 | 0 | 4 | 0 | 4 | 15 | 0 | 15 | 25 | 10 | 35 |
| 14 | 0 | 0 | 0 | 0 | 0 | 0 | 0 | 0 | 0 | 4 | 0 | 4 | 15 | 0 | 15 | 20 | 6 | 26 |
| 15 | 0 | 0 | 0 | 0 | 0 | 0 | 0 | 0 | 0 | 0 | 0 | 0 | 8 | 0 | 8 | 15 | 0 | 15 |
| 16 | 0 | 0 | 0 | 0 | 0 | 0 | 0 | 0 | 0 | 4 | 0 | 4 | 15 | 0 | 15 | 25 | 6 | 31 |
| 17 | 0 | 0 | 0 | 0 | 0 | 0 | 0 | 0 | 0 | 0 | 0 | 0 | 10 | 0 | 10 | 15 | 6 | 21 |
| 18 | 0 | 0 | 0 | 0 | 0 | 0 | 0 | 0 | 0 | 10 | 0 | 10 | 20 | 0 | 20 | 30 | 10 | 40 |
| 19 | 0 | 0 | 0 | 0 | 0 | 0 | 2 | 0 | 2 | 8 | 0 | 8 | 20 | 0 | 20 | 35 | 8 | 43 |
| 20 | 0 | 0 | 0 | 0 | 0 | 0 | 0 | 0 | 0 | 0 | 0 | 0 | 4 | 0 | 4 | 15 | 6 | 21 |
| 21 | 0 | 0 | 0 | 0 | 0 | 0 | 0 | 0 | 0 | 0 | 0 | 0 | 4 | 0 | 4 | 15 | 4 | 19 |
| 22 | 0 | 0 | 0 | 0 | 0 | 0 | 0 | 0 | 0 | 0 | 0 | 0 | 8 | 0 | 8 | 15 | 6 | 21 |
| 21 | 0 | 0 | 0 | 0 | 0 | 0 | 0 | 0 | 0 | 0 | 0 | 0 | 4 | 0 | 4 | 15 | 4 | 19 |
| 22 | 0 | 0 | 0 | 0 | 0 | 0 | 0 | 0 | 0 | 0 | 0 | 0 | 8 | 0 | 8 | 15 | 6 | 21 |
| 23 | 0 | 0 | 0 | 0 | 0 | 0 | 0 | 0 | 0 | 0 | 0 | 0 | 4 | 0 | 4 | 15 | 4 | 19 |
| 24 | 0 | 0 | 0 | 0 | 0 | 0 | 0 | 0 | 0 | 1 | 0 | 1 | 8 | 0 | 8 | 20 | 10 | 30 |
| 25 | 0 | 0 | 0 | 0 | 0 | 0 | 0 | 0 | 0 | 0 | 0 | 0 | 4 | 0 | 4 | 8 | 10 | 8 |
| 26 | 0 | 0 | 0 | 0 | 0 | 0 | 4 | 0 | 4 | 10 | 0 | 10 | 30 | 1 | 31 | 50 | 5 | 55 |
| 27 | 0 | 0 | 0 | 0 | 0 | 0 | 0 | 0 | 0 | 8 | 0 | 8 | 15 | 0 | 15 | 30 | 2 | 32 |
| 28 | 0 | 0 | 0 | 0 | 0 | 0 | 0 | 0 | 0 | 0 | 0 | 0 | 4 | 0 | 4 | 10 | 10 | 20 |
| 29 | 0 | 0 | 0 | 0 | 0 | 0 | 0 | 0 | 0 | 6 | 0 | 6 | 20 | 0 | 20 | 25 | 10 | 35 |
| 30 | 0 | 0 | 0 | 0 | 0 | 0 | 0 | 0 | 0 | 4 | 0 | 4 | 15 | 0 | 15 | 20 | 6 | 26 |
| 31 | 0 | 0 | 0 | 0 | 0 | 0 | 0 | 0 | 0 | 0 | 0 | 0 | 4 | 0 | 4 | 10 | 1 | 11 |
| 32 | 0 | 0 | 0 | 0 | 0 | 0 | 1 | 0 | 1 | 8 | 0 | 8 | 15 | 0 | 15 | 25 | 8 | 33 |
| 33 | 0 | 0 | 0 | 0 | 0 | 0 | 0 | 0 | 0 | 8 | 0 | 8 | 20 | 3 | 23 | 25 | 10 | 35 |
| 34 | 0 | 0 | 0 | 0 | 0 | 0 | 1 | 0 | 1 | 8 | 0 | 8 | 20 | 0 | 20 | 30 | 10 | 40 |
| 35 | 0 | 0 | 0 | 0 | 0 | 0 | 0 | 0 | 0 | 0 | 0 | 0 | 10 | 0 | 10 | 10 | 10 | 20 |
| 36 | 0 | 0 | 0 | 0 | 0 | 0 | 0 | 0 | 0 | 4 | 0 | 4 | 20 | 1 | 21 | 30 | 15 | 45 |
| 37 | 0 | 0 | 0 | 0 | 0 | 0 | 0 | 0 | 0 | 1 | 0 | 1 | 15 | 0 | 15 | 20 | 6 | 26 |
| 38 | 0 | 0 | 0 | 0 | 0 | 0 | 0 | 0 | 0 | 1 | 0 | 1 | 6 | 0 | 6 | 10 | 10 | 20 |
| 39 | 0 | 0 | 0 | 0 | 0 | 0 | 0 | 0 | 0 | 6 | 0 | 6 | 15 | 0 | 15 | 25 | 12 | 37 |
| 40 | 0 | 0 | 0 | 0 | 0 | 0 | 0 | 0 | 0 | 0 | 0 | 0 | 8 | 0 | 8 | 20 | 5 | 25 |
| 41 | 0 | 0 | 0 | 0 | 0 | 0 | 0 | 0 | 0 | 4 | 0 | 4 | 8 | 0 | 8 | 20 | 6 | 26 |
| 42 | 0 | 0 | 0 | 0 | 0 | 0 | 1 | 0 | 1 | 8 | 0 | 8 | 15 | 0.1 | 15.1 | 20 | 8 | 28 |
| 43 | 0 | 0 | 0 | 0 | 0 | 0 | 0 | 0 | 0 | 0 | 0 | 0 | 6 | 0 | 6 | 10 | 8 | 18 |
| 44 | 0 | 0 | 0 | 0 | 0 | 0 | 2 | 0 | 2 | 10 | 0 | 10 | 30 | 2 | 32 | 40 | 20 | 60 |
| 45 | 0 | 0 | 0 | 0 | 0 | 0 | 0 | 0 | 0 | 0 | 0 | 0 | 8 | 0 | 8 | 15 | 1 | 16 |
| 46 | 0 | 0 | 0 | 0 | 0 | 0 | 0.2 | 0 | 0.2 | 8 | 0 | 8 | 20 | 0 | 20 | 40 | 15 | 55 |
| 47 | 0 | 0 | 0 | 0 | 0 | 0 | 0 | 0 | 0 | 8 | 0 | 8 | 20 | 0 | 20 | 30 | 8 | 38 |
| 48 | 0 | 0 | 0 | 0 | 0 | 0 | 0 | 0 | 0 | 4 | 0 | 4 | 10 | 0 | 10 | 15 | 8 | 23 |
| 49 | 0 | 0 | 0 | 0 | 0 | 0 | 0 | 0 | 0 | 0 | 0 | 0 | 4 | 0 | 4 | 20 | 8 | 28 |
| 50 | 0 | 0 | 0 | 0 | 0 | 0 | 0 | 0 | 0 | 4 | 0 | 4 | 8 | 0 | 8 | 15 | 10 | 25 |
| 51 | 0 | 0 | 0 | 0 | 0 | 0 | 0 | 0 | 0 | 4 | 0 | 4 | 8 | 0 | 8 | 15 | 10 | 25 |
| 52 | 0 | 0 | 0 | 0 | 0 | 0 | 0 | 0 | 0 | 6 | 0 | 6 | 15 | 0 | 15 | 20 | 20 | 40 |
| 53 | 0 | 0 | 0 | 0 | 0 | 0 | 0 | 0 | 0 | 4 | 0 | 4 | 12 | 0 | 12 | 20 | 10 | 30 |
| 54 | 0 | 0 | 0 | 0 | 0 | 0 | 0 | 0 | 0 | 1 | 0 | 1 | 10 | 0 | 10 | 20 | 8 | 28 |
| 55 | 0 | 0 | 0 | 0 | 0 | 0 | 0.2 | 0 | 0.2 | 8 | 0 | 8 | 15 | 0 | 15 | 25 | 10 | 35 |
| 56 | 0 | 0 | 0 | 0 | 0 | 0 | 0 | 0 | 0 | 4 | 0 | 4 | 15 | 0 | 15 | 25 | 10 | 35 |
| 57 | 0 | 0 | 0 | 0 | 0 | 0 | 0 | 0 | 0 | 1 | 0 | 1 | 8 | 0 | 8 | 15 | 8 | 23 |
| 58 | 0 | 0 | 0 | 0 | 0 | 0 | 0 | 0 | 0 | 8 | 0 | 8 | 15 | 0 | 15 | 30 | 10 | 40 |
| 59 | 0 | 0 | 0 | 0 | 0 | 0 | 0.2 | 0 | 0.2 | 10 | 0 | 10 | 40 | 0 | 40 | 50 | 6 | 56 |
| 60 | 0 | 0 | 0 | 0 | 0 | 0 | 0 | 0 | 0 | 4 | 0 | 4 | 10 | 0 | 10 | 25 | 8 | 33 |
| 61 | 0 | 0 | 0 | 0 | 0 | 0 | 1 | 0 | 1 | 15 | 0 | 15 | 40 | 0 | 40 | 55 | 3 | 58 |
| 62 | 0 | 0 | 0 | 0 | 0 | 0 | 0 | 0 | 0 | 0 | 0 | 0 | 2 | 0 | 2 | 10 | 8 | 18 |
| 63 | 0 | 0 | 0 | 0 | 0 | 0 | 0 | 0 | 0 | 0 | 0 | 0 | 4 | 0 | 4 | 12 | 8 | 20 |
| 64 | 0 | 0 | 0 | 0 | 0 | 0 | 0 | 0 | 0 | 0 | 0 | 0 | 8 | 0 | 8 | 20 | 10 | 30 |
| 65 | 0 | 0 | 0 | 0 | 0 | 0 | 0 | 0 | 0 | 0 | 0 | 0 | 6 | 0 | 6 | 20 | 4 | 24 |
| 66 | 0 | 0 | 0 | 0 | 0 | 0 | 0 | 0 | 0 | 4 | 0 | 4 | 15 | 0 | 15 | 25 | 6 | 31 |
| 67 | 0 | 0 | 0 | 0 | 0 | 0 | 0 | 0 | 0 | 1 | 0 | 1 | 12 | 0 | 12 | 35 | 4 | 39 |

Table 3-continued

| Term for dipping | 2 months | | | 4 months | | | 6 months | | | 8 months | | | 10 months | | | 12 months | | |
|---|---|---|---|---|---|---|---|---|---|---|---|---|---|---|---|---|---|---|
| Adhered shellfish and algae Compound No. | S | A | T | S | A | T | S | A | T | S | A | T | S | A | T | S | A | T |
| non-treated | 20 | 35 | 55 | 30 | 55 | 85 | 55 | 45 | 100 | 65 | 35 | 100 | 80 | 20 | 100 | 80 | 20 | 100 |

S : Shellfish
A : Algae
T : Total

Shellfish-Algae Inhibiting Test for Fishing Net 1

(1) Preparation of composition

The compound No. 1 of N-phenylmaleimide was uniformly mixed with the following components to prepare a resin solution.

| Compound No. 1 | 8 wt. % |
|---|---|
| Chlorinated rubber | 5 wt. % |
| Rosin | 2 wt. % |
| Toluene | 85 wt. % |
| Total | 100 wt. % |

(2) Treatment of Fishing net

A fishing net having 11 knots (stitch of 3.03 cm) prepared by using polyamide filaments (manufactured by Toray Co. Ltd.), was immersed into the resin solution (1) and was dried for 12 hours in air.

Shellfish-Algae Inhibiting Test for Fishing Net 2

(1) Preparation of Composition

The Compound No. 3 of N-(3-chlorophenyl)maleimide was uniformly mixed with the following components to prepare a resin solution.

| Compound No.3 | 5 wt. % |
|---|---|
| Vinyl resin | 5 wt. % |
| Rosin | 5 wt. % |
| Xylene | 85 wt. % |
| Total | 100 wt. % |

(2) Treatment of Fishing Net

In accordance with the treatment of fishing net 1-(2), the fishing net was treated with the resin solution 2-(1).

Test for Treated Fishing Net 3

The shellfish-algae inhibiting tests were carried out by using various treated fishing nets treated with resin solutions containing various N-arylmaleimides is accordance with the test for treatment of fishing net 1.

(1) Test Method

Each sample having a size of 50 × 50 cm cut from the treated fishing nets, and was supported by each steel frame having a size of 60 × 60 cm and was dipped into sea from a raft by dipping at a depth of 1.5 m.

(2) Results

The samples dipped in sea were pulled up for each specific terms of 1, 2, 3, 4, 5 and 6 months.

The conditions adhereing of shellfish and algae such as Hydrozoa, Styela, Bugula, Ulva, Enteromorpha, Ectocarpus, etc.. were observed and the ratio of the weight increases of the nets were measured.

The results are shown in Table 4. The ratings are given as follows.

− no adhesion
± spots
+ small amount in adhesion for the whole surface
++ large amount in adhesion for whole surface
+++ large amount for clogging whole meshes.

The ratio of weight increase of the net is shown by percent of each weight increase to the original weight of the net. The weights were measured at 1 hour after pulling up the net from the sea.

Table 4

| Compound No. | Adhesion of algae (Month) | | | | | | Ratio of weight increase of net (%) (Month) | | | | | |
|---|---|---|---|---|---|---|---|---|---|---|---|---|
| | 1 | 2 | 3 | 4 | 5 | 6 | 1 | 2 | 3 | 4 | 5 | 6 |
| 1 | − | − | − | ± | + | ++ | 5 | 9 | 6 | 13 | 24 | 50 |
| 2 | − | − | − | ± | + | ++ | 3 | 4 | 9 | 10 | 25 | 69 |
| 3 | − | − | − | − | − | ± | 3 | 3 | 4 | 3 | 6 | 15 |
| 4 | − | − | − | + | ± | + | 4 | 4 | 5 | 20 | 15 | 42 |
| 5 | − | − | − | − | − | − | 3 | 5 | 5 | 3 | 6 | 9 |
| 6 | − | − | − | ± | ± | ± | 3 | 9 | 8 | 12 | 19 | 22 |
| 7 | − | − | − | − | − | − | 10 | 8 | 10 | 9 | 15 | 9 |
| 8 | − | − | − | − | − | − | 3 | 9 | 15 | 5 | 15 | 13 |
| 9 | − | − | − | − | − | ± | 4 | 10 | 9 | 8 | 13 | 25 |
| 10 | − | − | − | − | − | ± | 8 | 8 | 8 | 16 | 10 | 16 |
| 11 | − | − | − | − | − | − | 3 | 4 | 15 | 8 | 8 | 8 |
| 12 | − | − | − | − | − | − | 4 | 3 | 5 | 2 | 6 | 9 |
| 13 | − | − | − | − | − | − | 3 | 5 | 10 | 9 | 13 | 15 |
| 14 | − | − | − | − | − | − | 3 | 9 | 15 | 11 | 13 | 10 |
| 15 | − | − | − | − | − | − | 7 | 15 | 15 | 6 | 9 | 15 |
| 16 | − | − | − | − | − | − | 6 | 10 | 10 | 21 | 9 | 9 |
| 17 | − | − | − | − | − | ± | 3 | 4 | 4 | 6 | 6 | 15 |
| 18 | − | − | − | ± | ± | + | 3 | 6 | 10 | 10 | 15 | 33 |
| 19 | − | − | − | + | ++ | ++ | 3 | 9 | 6 | 18 | 29 | 91 |
| 20 | − | − | − | − | − | − | 7 | 7 | 17 | 22 | 10 | 10 |
| 21 | − | − | − | − | − | − | 3 | 3 | 15 | 12 | 12 | 9 |
| 22 | − | − | − | − | − | − | 4 | 3 | 5 | 4 | 6 | 10 |
| 23 | − | − | − | − | − | − | 4 | 3 | 5 | 4 | 9 | 10 |
| 24 | − | − | − | − | − | ± | 4 | 3 | 5 | 10 | 9 | 18 |
| 25 | − | − | − | − | − | − | 5 | 10 | 13 | 8 | 20 | 13 |
| 26 | − | − | ± | + | ± | ++ | 3 | 9 | 16 | 28 | 69 | 120 |
| 27 | − | − | − | − | ± | + | 5 | 5 | 6 | 5 | 17 | 40 |
| 28 | − | − | − | − | ± | − | 6 | 10 | 15 | 8 | 25 | 8 |
| 291 | − | − | − | − | ± | + | 3 | 9 | 6 | 13 | 22 | 44 |

Table 4-continued

| Compound No. | Adhesion of algae (Month) 1 | 2 | 3 | 4 | 5 | 6 | Ratio of weight increase of net (%) (Month) 1 | 2 | 3 | 4 | 5 | 6 |
|---|---|---|---|---|---|---|---|---|---|---|---|---|
| 30 | − | − | − | − | ± | + | 4 | 5 | 13 | 6 | 25 | 50 |
| 31 | − | − | − | − | − | − | 3 | 3 | 3 | 4 | 9 | 6 |
| 32 | − | − | − | ± | + | ++ | 3 | 9 | 13 | 13 | 30 | 71 |
| 33 | − | − | − | ± | + | ++ | 3 | 4 | 4 | 15 | 29 | 51 |
| 34 | − | − | − | + | ++ | ++ | 3 | 3 | 3 | 14 | 40 | 95 |
| 35 | − | − | − | ± | + | ++ | 3 | 3 | 4 | 16 | 20 | 50 |
| 36 | − | − | ± | ± | + | ++ | 3 | 8 | 7 | 24 | 31 | 62 |
| 37 | − | − | − | ± | + | ++ | 5 | 4 | 10 | 13 | 25 | 65 |
| 38 | − | − | − | − | ± | + | 7 | 10 | 18 | 13 | 25 | 40 |
| 39 | − | − | − | ± | + | ++ | 9 | 15 | 18 | 19 | 40 | 73 |
| 40 | − | − | − | ± | + | ++ | 6 | 3 | 8 | 19 | 42 | 59 |
| 41 | − | − | − | ± | ± | + | 3 | 10 | 14 | 14 | 14 | 49 |
| 42 | − | − | ± | − | ± | + | 7 | 8 | 15 | 8 | 21 | 48 |
| 43 | − | − | − | + | +30 | ++ | 3 | 4 | 3 | 20 | 45 | 98 |
| 44 | − | − | ± | ± | + | ++ | 9 | 15 | 15 | 15 | 25 | 69 |
| 45 | − | − | − | − | − | − | 3 | 6 | 7 | 9 | 6 | 9 |
| 46 | − | − | ± | + | ++ | ++ | 3 | 9 | 15 | 23 | 51 | 110 |
| 47 | − | − | ± | ± | ± | + | 5 | 8 | 15 | 20 | 15 | 50 |
| 48 | − | − | − | ± | ± | + | 5 | 8 | 16 | 16 | 19 | 39 |
| 49 | − | − | − | − | − | + | 9 | 8 | 15 | 14 | 10 | 26 |
| 50 | − | − | ± | + | + | ++ | 5 | 4 | 18 | 25 | 24 | 29 |
| 51 | − | − | − | − | ± | + | 4 | 6 | 13 | 12 | 21 | 50 |
| 52 | − | − | − | ± | + | ++ | 5 | 8 | 12 | 15 | 28 | 79 |
| 53 | − | − | ± | ± | + | ++ | 5 | 8 | 15 | 19 | 35 | 85 |
| 54 | − | − | − | − | − | − | 5 | 8 | 8 | 11 | 9 | 18 |
| 55 | − | − | − | ± | ± | + | 4 | 8 | 7 | 15 | 10 | 55 |
| 56 | − | − | ± | + | + | ++ | 6 | 7 | 16 | 28 | 24 | 60 |
| 57 | − | − | − | ± | ± | ++ | 4 | 5 | 9 | 24 | 51 | 120 |
| 58 | − | − | − | − | + | ++ | 5 | 8 | 13 | 12 | 25 | 116 |
| 59 | − | − | ± | + | ++ | ++ | 7 | 9 | 15 | 25 | 63 | 161 |
| 60 | − | − | ± | + | ++ | ++ | 4 | 4 | 9 | 15 | 45 | 129 |
| 61 | − | − | ± | + | ++ | ++ | 4 | 5 | 10 | 23 | 45 | 131 |
| 62 | − | − | − | − | − | − | 3 | 6 | 3 | 15 | 8 | 9 |
| 63 | − | − | − | − | ± | + | 3 | 3 | 4 | 3 | 18 | 40 |
| 64 | − | − | ± | + | ++ | ++ | 3 | 9 | 19 | 31 | 70 | 145 |
| 65 | − | − | ± | + | ++ | ++ | 3 | 3 | 16 | 25 | 44 | 121 |
| 66 | 31 | − | + | + | + | ++ | 9 | 8 | 21 | 28 | 46 | 130 |
| 67 | − | − | − | ± | + | ++ | 6 | 6 | 11 | 19 | 31 | 82 |
| Non-treated | − | ± | + | ++ | +++ | +++ | 3 | 11 | 44 | 51 | 161 | 395 |

What is claimed is:

1. A method of inhibiting adhesion of shellfish and algae on a fish net or a ship bottom or an apparatus in water which comprises coating thereon a composition comprising a resin, a medium and from 5-80 wt.% thereof of a N-aryl-maleimide having the formula:

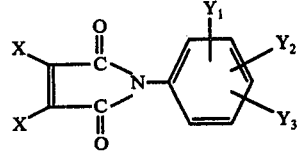

wherein X represents hydrogen or halogen atom; $Y_1$ represents hydrogen or halogen atom or alkyl, lower alkoxy, nitro, hydroxyl, alkoxycarbonyl, carboxyl, phenyl, phenylamino, alkenyl, thiocyano, sulfone, acetylamino or sulfamoyl group; $Y_2$ represents hydrogen or halogen atom or alkyl, lower alkoxy, nitro or hydroxyl group and $Y_3$ represents hydrogen or halogen atom or dialkylamino group.

2. The process of claim 1, wherein the medium is an organic solvent.

* * * * *